US006441050B1

(12) United States Patent
Chopra

(10) Patent No.: US 6,441,050 B1
(45) Date of Patent: Aug. 27, 2002

(54) PALATABLE ORAL COENZYME Q LIQUID

(76) Inventor: Raj K. Chopra, 704 Demott Ct., Westbury, NY (US) 11590

(*) Notice: Subject to any disclaimer, the term of this patent is extended or adjusted under 35 U.S.C. 154(b) by 0 days.

(21) Appl. No.: 09/650,487

(22) Filed: Aug. 29, 2000

(51) Int. Cl.⁷ .................. A61K 31/12; A61K 31/075; A61K 47/00; A01N 31/14
(52) U.S. Cl. ................. 514/675; 514/718; 424/439
(58) Field of Search .................. 424/439; 514/675, 514/718

(56) References Cited

U.S. PATENT DOCUMENTS

| | | | |
|---|---|---|---|
| 4,599,232 A | 7/1986 | Bertelli |
| 4,602,039 A | 7/1986 | Cavazza |
| 4,929,437 A | 5/1990 | Tobert |
| 4,933,165 A | 6/1990 | Brown |
| 5,082,650 A | 1/1992 | Folkers et al. |
| 5,316,765 A | 5/1994 | Folkers et al. |
| 6,045,826 A | 4/2000 | Borowy-Boroeski et al. |
| 6,056,971 A | 5/2000 | Goldman |
| 6,126,943 A | 10/2000 | Cheruvanky et al. |

FOREIGN PATENT DOCUMENTS

| | | | |
|---|---|---|---|
| FR | 2514346 | * | 4/1983 |
| GB | 1533084 | * | 11/1978 |
| GB | 2157171 | * | 10/1985 |

OTHER PUBLICATIONS

"Cardiology" edited by J. Dereck Jeffers and Fulvio Bruno: McGraw–Hill International Ltd., England. Chapter 46 and 48, 1999.
Andrée et al. "An Endogenous Lipid–Soluble Antioxidant in Animal Tissues", in Biological Systems, edited by Gilbert and Colton. Kluwer Academic / Pienum Publishers, New York, pp. 453–477, 1999.
A F. Wagner and K. Folkers. "Quasivitamins", pp. 421–455.

* cited by examiner

Primary Examiner—Alton Pryor
(74) Attorney, Agent, or Firm—Henry D. Coleman; Coleman, Sudol, Sapone, P.C.

(57) ABSTRACT

The present invention relates to a composition in pharmaceutical dosage form of coenzyme Q or ubiquinol which can be administered to children in an oral dosage form as a pleasant-tasting liquid. The dosage form comprises an effective amount of coenzyme Q or ubiquinol ranging from about 0.05% to about 10%, more preferably about 1% to about 7.5% by weight of the composition in combination with a minor amount of a polysorbate surfactant such as a Tween™ surfactant, most preferably, polysorbate 80, a major amount of a vegetable oil or triglyceride, in further combination with an amount of phospholipid such as hydroxylated lecithin effective to maintain ubiquinone/ubiquinol in hydrosoluble form and to substantially enhance the palatability of ubiquinone or ubiquinol in combination with a sweetener solution as well as an amount of water preferably ranging from about 5% to about 45% by weight.

35 Claims, No Drawings

PALATABLE ORAL COENZYME Q LIQUID

FIELD OF THE INVENTION

The present invention relates to oral compositions comprising coenzyme Q (ubiquinone) or ubiquinol (a reduced form of coenzyme Q) in a liquid form which provides enhanced bioavailability and is palatable to patients, especially children.

BACKGROUND OF THE INVENTION

Syrups, elixirs, solutions, and suspensions are traditional dosage forms for oral medication and are particularly useful for certain applications where children represent the main target pool of patients. Liquid formulations, at least with respect to a target pool of children, represents a favorable approach for enhancing patient compliance. However, the sine qua non for enhancing patient compliance via an oral route is a formulation with favorable palatability.

Coenzyme Q (ubiquinone), a dietary supplement, is a vitamin-like substance which is used to treat congestive heart failure and other cardiac problems, including heart ailments and diseases such as congestive heart failure, as well as a number of other conditions including high blood pressure, mitochochondrial disorders, including mitochondrial encephalomyopathy, anoxia, lactic acidosis, strokelike symptoms, neurodegenerative diseases, Kearns-Sayre syndrome and Alper's disease, among others. Coenzyme Q is the best known of a group of lipophilic quinones which have the capacity to transfer reducing equivalents or electrons within a lipid phase of cellular membranes. Reduced benzoquinones in general are effective reductants for oxygen or lipid radicals. Early studies showed that reduced coenzyme Q is an effective antioxidant. See, Mellors and Tappel, 1996, J. Biol. Chem., 241: 4353–4356. Reduced coenzyme Q now appears to function as part of a complex chain of antioxidant activity.

An important role of coenzyme Q can be in reduction of radicals of α-tocopherol and ascorbate formed when these antioxidants are oxidized by oxygen or carboxyl radicals. There are no enzymes for direct reduction of tocopheryl radical or external ascorbate radical, but there are enzymes in all membranes which can reduce coenzyme Q and the reduced coenzyme Q can reduce the tocopheryl or ascorbate radicals to restore tocopherol or ascorbate. Without the support of enzymes to reduce coenzyme Q, the reduced coenzyme Q would not be a very effective antioxidant because the semiquinone formed by interaction with lipid or oxygen radicals is readily autooxidized with formation of a superoxide radical.

There are several problems with the administration of Coenzyme Q and its reduced form, ubiquinol. First, Coenzyme Q is essentially insoluble in water and ubiquinol is only slightly better. Second, in general, Coenzyme Q and ubiquinol are poorly absorbed, although their bioavailability may be enhanced in hydrosoluble form. Notwithstanding the increased bioavailability of coenzyme Q and especially, ubiquinol, in hydrosoluble form, the taste of the hydrosoluble form of coenzyme Q and ubiquinol is such that formulation as a pleasant tasting liquid for children as an oral dosage form is simply not possible. This is especially problematic for treating children with coenzyme Q and/or ubiquinol in rare orphan diseases such as mitochondrial cytopathies and other disease states or conditions.

Objects of the Invention

It is therefore an object of the present invention to provide a palatable form of Coenzyme Q (ubiquinone) or ubiquinol which can be administered to children in an oral dosage form as a pleasant-tasting liquid.

It is another object of the invention to provide a method for treating children for mitochondrial cytopathies and other diseases and conditions using an oral dosage form which is palatable to children and promotes high bioavailability of coenzyme Q or ubiquinol.

It is a further object of the invention to provide a method for making an oral dosage form of ubiquinone/ubiquinol more palatable.

These and/or other objects of the invention may be readily gleaned from a description of the invention which follows.

SUMMARY OF THE INVENTION

The present invention relates to a composition in pharmaceutical dosage form of coenzyme Q or ubiquinol which can be administered to children in an oral dosage form as a pleasant-tasting liquid. The dosage form comprises an effective amount of coenzyme Q or ubiquinol ranging from about 0.05% to about 10%, more preferably about 1% to about 7.5% by weight of the composition in combination with a minor amount of a polysorbate surfactant such as a Tween™ surfactant, most preferably, polysorbate 80, a major amount of a vegetable oil or triglyceride, in further combination with an amount of phospholipid such as hydroxylated lecithin effective to substantially enhance the palatability of ubiquinone or ubiquinol in combination with a sweetener solution as well as an amount of water preferably ranging from about 5% to about 45% by weight.

In addition to the above components, compositions according to the present invention may optionally comprise solvents, flavorings and optionally, at least one additional surfactant such as a Span surfactant in relatively minor amounts (i.e., in amounts which do not substantially impact the ability of the other components to work together to form a palatable liquid oral dosage form). In the case of the inclusion of ubiquinol, effective amounts of a lipid soluble reducing agent is preferably included in compositions according to the present invention.

DETAILED DESCRIPTION OF THE INVENTION

The term "coenzyme Q" or "ubiquinone" is used throughout the present specification to describe a group of lipid soluble benzoquinones involved in electron transport in mitochondrial preparations, i.e., in the oxidation of succinate or reduced nicotine adenine dinucleotide (NADH) via the cytochrome system. According to the existing dual system of nomenclature, the compounds can be described as: coenzyme $Q_n$, where n is 1–12 or ubiquinone (x) in which x designates the total number of carbon atoms in the side chain and can be any multiple of 5. Differences in properties are due to to the difference in the chain length. The preferred ubiquinone for use in the present invention is coenzyme $Q_{10}$.

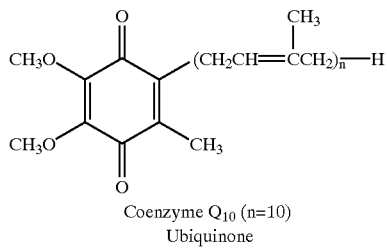

Coenzyme $Q_{10}$ (n=10)
Ubiquinone

The term "ubiquinol" is used throughout the specification to describe the reduced form of coenzyme Q which is used as an active ubiquinone in compositions according to the present invention. In ubiquinol, the quinone ring of coenzyme Q is reduced such that the structure of the compound appears as set forth below. In ubiquinol, n is preferably 10 and is derived from coenzyme $Q_{10}$ by the reduction of coenzyme $Q_{10}$.

The amount of ubiquinone/ubiquinol which is included in compositions according to the present invention ranges from about 0.1% to about 10% (preferably, no more than about 7.5% by weight and even more preferably no more than about 5% by weight of the final liquid composition). The amount of ubiquinol which is included in compositions according to the present invention ranges from about 0.1 to about 10.0 times, more preferably about 1 to about 3 times the amount (in weight percent) of the lipid soluble reducing agent which is included in compositions according to the present invention.

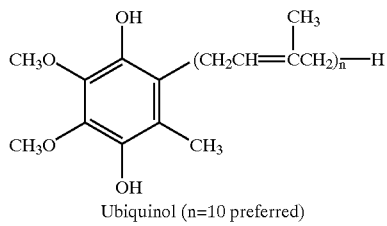

Ubiquinol (n=10 preferred)

The term "surfactant" or "emulsifier" is used interchangeably to describe additives to compositions according to the present invention. Surfactants are solubilizers which are used to promote the solubility of the ubiquinone/ubiquinol. These are to be used in combination with a triglyceride or vegetable oil and a phospholipid. Polysorbate surfactants (Tween™) are clearly preferred as primary surfactants, but they may be supplemented in the present compositions with minor amounts of secondary surfactants, for example the Span™ surfactants. The amount of surfactant used in the present invention ranges from about 0.1% to about 35% by weight, more preferably about 1.5% to about 25%, preferably about 2% to about 15% by weight. Surfactants for use in the present invention are pharmaceutically acceptable and include, for example, the polysorbate surfactants as primary surfactants and complex esters or ester-ethers prepared from hexahydric alcohols, alkylene oxides and fatty acids (the Span™ surfactants) as secondary surfactants. Surfactants which exist in the liquid state at temperatures at or less than formulation temperature (generally, about 80° C. or less, more preferably about 50–65°) are preferred because they can also function as co-solvents or co-solubilizers in the present compositions. The preferred surfactants for use in the present invention include Tween™ (polysorbate) surfactants as primary surfactants and Span™ surfactants as optional secondary surfactants, which are well-known in the art for use as stabilizers, surfactants, emulsifiers and thickeners in foods, cosmetics and medical products, among others. Preferred surfactants are those which are in a liquid state during formulation such that the surfactant may also function as a solubilizer (i.e., it has solvent-like properties).

In the present invention, the use of a polysorbate (Tween™) surfactant is preferred, with a mixture of Span™ and Tween™ surfactants, being optional.

The Tween™ or polysorbate type surfactants are oleate esters of sorbitol and its anhydrides copolymerized with a number of moles of ethylene oxide per mole of sorbitol and sorbitol anhydride. The Tween™ surfactants are soluble or well dispersible in water. Preferred Tween™ surfactants include a sorbitan mono-9-octadecenoate poly(oxy-1,2-etheandiyl) derivative otherwise known as Tween™ 80 or Polysorbate 80.

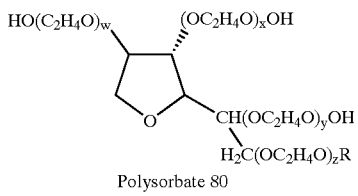

Polysorbate 80

The sum of w,x,y and z is 20 and $R=C_{17}H_{33}CO$

The Span™ surfactants, which may be optionally included in the present compositions of the present invention as secondary surfactants (the polysorbate surfactants are the preferred primary surfactants), are partial esters of common fatty acids, such as lauric acid, palmitic acid, stearic acid and oleic acids and hexitol anhydrides such as hexitans and hexides, derived from sorbitol (see below). In the case of Span 20, the sorbitan fatty ester is based upon laurate ester. In the case of Span 60, the ester is based upon stearate ester and in the case of Span 80, the ester is based upon oleic ester. The hydrophilic character of the Span™ surfactants is supplied by free hydroxyl and oxyethylene groups, while the lipophilic character is provided by the long chain fatty groups. The Span™ surfactants tend to be oil soluble and dispersible or insoluble in water. However, these surfactants work in tandem with the more water soluble polyhydric alcohol to provide a soluble ubiquinol for soft gel formulations according to the present invention. The use of Span 80 in formulating compositions according to the present invention is preferred.

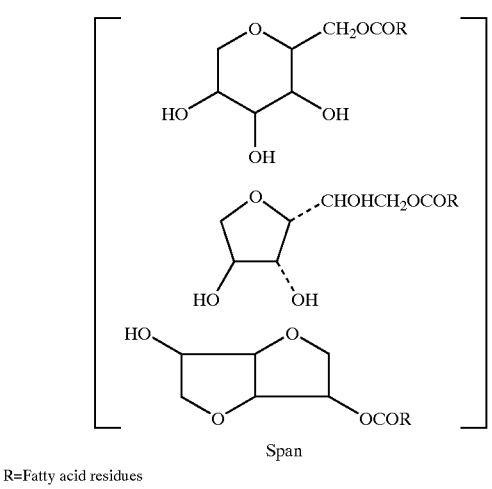

Span

R=Fatty acid residues

The term "palatable" is used throughout the specification to describe compositions according to the present invention with respect to their taste. Palatable compositions according to the present invention are those compositions which are agreeable in taste or are otherwise pleasant-tasting.

The term "reducing agent" is used throughout the specification to describe pharmaceutically acceptable hydrophobic reducing agents which are added to the compositions according to the present invention in effective amounts to convert ubiquinone to ubiquinol during manufacturing and/ or to substantially reduce oxidation of ubiquinol to ubiquinone (Coenzyme Q) during manufacturing and/or storage of the compositions according to the present invention. Preferred reducing agents include any reducing agent which is compatible with ubiquinol in pharmaceutical form and is capable of providing the requisite reducing activity to stabilize ubiquinol for storage and is hydrophobic (lipophilic) and otherwise soluble in the triglycerides used in the present invention. Preferably, the reducing agent is a lipid soluble reducing agent for example, α-tocopherol (vitamin E), tocopherol esters, ascorbate esters such as ascorbyl palmitate, among others, alpha carotene and β-carotene, lycopene, flavonoids, riboflavin, curcuminoids, retinol (Vitamin A), retinoic acid, retinoic acid esters, retinol acetate, retinal and related reducing agents, preferably those which may also be used as additives in dietary supplements. While not being limited by way of theory, it is believed that the inclusion of a lipid soluble reducing agent, including lipid soluble reducings agents which are also biologically active, is preferred because such a composition provides a reducing agent which will most greatly compatibilize with the ubiquinol and the triglycerides (vegetable oil), yet create an emulsion which will mask the rather unpleasant taste of the ubiquinol.

Preferred lipid soluble reducing agents are those which are soluble in the triglycerides or vegetable oil and the hydrophobic portion of the phospholipids which are used in the present invention. In certain embodiments, the inclusion of a solvent as otherwise described herein optionally may be added in minor amounts A lipid soluble reducing agent for use in the present invention comprises about 0.05% to about 15% by weight of the composition, more preferably about 1% to about 7.5% by weight of the final composition. The ratio of reducing agent to ubiquinol in compositions according to the present invention generally ranges from about 1:10 to about 10:1, more preferably about 1:5 to about 5:1, more preferably about 1:1 to about 3:1. In embodiments according to the present invention which rely on an in situ preparation of ubiquinol from ubiquinone, the amount of reducing agent which is used in the reduction reaction is preferably an excess of that amount required for the reduction reaction on a weight percentage basis. Additional reducing agent may be incorporated into the final formulations after the in situ preparation of ubiquinol from ubiquinone in order to promote the storage stability of the ubiquinol.

It is believed that effective concentrations of reducing agents convert substantially all of the ubiquinone to ubiquinol during manufacturing in an efficient method for preparing ubiquinol. In other embodiments, effective concentrations of reducing agents also prevent ubiquinol from being oxidized to ubiquinone, or alternatively reduce any ubiquinone which has been oxidized from ubiquinol during storage of the compositions according to the present invention.

The term "phospholipid" as used herein shall mean any suitable material of a lipid like, but amphipathic nature which is a phospholipid, and which preferably has a hydrophobic chain at one end of the molecule and a hydrophilic, charged (anionic) portion at the other end of the molecule. Hydroxylated phospholipids pursuant to the present invention are preferred. In the present invention, the phospholipid is used to help promote the solubility of ubiquinone or ubiquinol within an aqueous solution to be administered orally in combination with a polysorbate surfactant and a triglyceride or oil, to maintain the ubiquinone/ubiquonol in hydrosoluble form in order to promote the bioavailability of the active and promotes the "masking" of the ubiquinone/ ubiquinol and other components (especially, the polysorbate surfactant) from the patient's taste receptors in a manner such that the composition has a vastly improved palatability. Although any number of phospholipids can be used in the present invention, preferred phospholipids include, for example, phosphatidylcholine (PC), phosphatidylethanolamine (PE), distearoylphosphatidylcholine (DSPC), phosphatidylserine (PS), phosphatidylglycerol (PG), phosphatidic acid (PA), phosphatidylinositol (PI), sphingomyelin (SPM), and the like, alone or in combination. The phospholipids can be synthetic or derived from natural sources such as egg or soy, but are preferably natural or are obtained from natural products. Some synthetic phospholipids which can be used in the present invention include, for example, dimyristoylphosphatidylcholine (DMPC) and dimyristoylphosphatidylglycerol (DMPG). Within the class of phospholipids include the phosphoglycerides, which are generally related to triglycerides in that they contain two fatty acid residues and a phosphate ester (generally, a diester) group off of the three hydroxyl groups of glycerine.

Phospholipids are preferably included in the present compositions in amounts effective to mask the taste of hydrosoluble ubiquinone/ubiquinol. This amount generally falls within the range from about 0.5% to about 20%, more preferably about 1% to about 15%, even more preferably about 1% to about 10% by weight of the final composition. While not being liimited by way of theory, it is believed that the inclusion of the phospholipid is an important feature in the present invention, inasmuch it is the phospholipid which is believed to surround or encapsulate the ubiquinone and triglyceride in an aqueous medium, thus maintaining the ubiquinone/ubiquinol in hydrosoluble form within phospholipid enapsulated micelles or related structures which maintain the fat soluble components as well as the polysorbate surfactant in hydrosoluble form for enhanced bioavailability of the active, and limiting or even eliminating the chance that foul-tasting components will come into contact with the patient's taste receptors during oral administration. It is an unexpected result that the present compositions would be so effective in providing a hydrosoluble form of ubiquinone/ubiquinol with enhanced bioavailibility from a palatable oral liquid form.

The term "hydrosoluble" is used throughout the specification to describe a formulation which is in a liquid or liquid-like form and contains sufficient surfactant as well as other components such that when the composition comes into contact with water or an aqueous medium such as gastric juices, the composition will maintain itself in the form of an emulsion or an emulsion-like form, rather than precipitating out of solution. It is the hydrosoluble form of the present invention, which is administered orally, in the form of a liquid, which produces the unexpectedly high bioavailability of ubiquinone/ubiquinol from orally administered compositions according to the present invention.

The term "patient" or "subject" is used throughout the specification to describe an animal, generally a human, to whom administration of the compositions according to the present invention is provided. In certain preferred aspects according to the present invention, a patient is a child ranging in age from a neonate to a teenager.

The term "effective amount" is used throughout the specification to describe concentrations or amounts of compounds according to the present invention which are used to produce a favorable result, whether that result relates to a composition's therapeutic or physiological effect or its ability to function for an alternative intended use, for example, a phospholipid which promotes formation and maintaining of ubiquinone/ubiquinol in hydrosoluble form or masks the taste of ubiquinone/ubiquinol or other components within the composition or a reducing agent converting ubiquinone to ubiquinol during manufacturing or to prevent and/or limit the change in or oxidation of the ubiquinol or to function as a solvent in compositions according to the present invention.

The terms "triglycerides" and "vegetable oil" are used synonymously throughout the specification to describe an additive in compositions according to the present invention which may serve as a solubilizer or a compatibilizer of the ubiquinone/ubiquinol with the other components of the present invention. This term is used as it is used by those of ordinary skill in the art, wherein fatty acids are esterifed at the free hydroxyl positions of glycerine, producing triglycerides, which are also the primary component of vegetable oils. Preferred triglycerides for use in the present compositions include vegetable oils including "medium chain triglycerides", which are tri-fatty esters of glycerol wherein the chain length of the fatty acids range from about 10–18 carbon units. Triglycerides are used as solubilizers, diluents and excipients, to compatabilize the formulations and promote uniformity. They are also integral to solubilization of the ubiquinone/ubiquinol and further compatabilization with the phospholipid component of the present invention which results in the masking of the unpleasant taste of ubiquinone/ubiquinol.

Vegetable oils for use in the present invention may include, for example, tri-glycerides which may be natural or synthetic (derived from esterification of glycerol and at least one organic acid, saturated or unsaturated, such as for example, such as butyric, caproic, palmitic, stearic, oleic, linoleic or linolenic acids, among numerous others, preferably a fatty organic acid, comprising between 8 and 26 carbon atoms). Glyceride esters for use in the present invention include vegetable oils derived chiefly from vegetables, seeds or nuts and include, for example, soybean, sunflower, safflower and cottonseed oil; non-drying oils, for example castor and coconut oil; and other oils, such as, for example, palm oil. Hydrogenated vegetable oils also may be used in the present invention. Animal oils are also contemplated for use as glyceride esters and include, for example, fats such as tallow, lard and stearin and liquid fats, such as fish oils, fish-liver oils and other animal oils, including sperm oil, among numerous others. In addition, a number of other oils may be used, including $C_{12}$ to $C_{30}$ (or higher) fatty esters (other than the glyceride esters, which are described above) or any other pharmaceutically acceptable triglyceride.

The term "sweetener" is used throughout the specification to describe a sweetener, preferably an aqueous solution of a natural or artificial sweetener, which is added to compositions according to the present invention in order to render the composition more palatable. Sweeteners according to the present invention include for example, aspartame, saccharin, cyclamates, sucralose, among numerous other synthetic sweeteners, as well as sugar based sweeteners such as sucrose/water solutions (USP sucrose syrup, about 85% by weight sucrose and about 15% by weight water), maltose, corn syrup, fructose syrup and related fruit syrup sweeteners, isomalt and sugar alcohols including xylitol, mannitol, maltitol, and sorbitol solutions, among others. The amount of sweetener used in the present compositions ranges from about 0.05% to about 65% or more by weight, depending upon the strength of the sweetener used. Preferred sweeteners include the sugar based sweeterners, such as sucrose syrup and corn syrup.

The term "solvent" is used throughout the specification to describe a liquid into which the ubiquinol and reducing agent is at least partially solubilized, generally in combination with the surfactant and triglyceride as otherwise described herein, is added. Solvents for use in the present invention include any hydrophilic solvent which is pharmaceutically acceptable and which can be used as a solvent, which alone, or in combination with surfacants as otherwise described herein, dissolves ubiquinol and the reducing agent. Preferred solvents for use in the present invention include ethanol and "polyhydric alcohols" a term which is used throughout the present invention to describe any one or more pharmaceutically compatible polyhydric alcohol compounds which are used to solubilize ubiquinol and the reducing agent used in compositions according to the present invention. Polyhydric alcohols which may be used in the present invention include, for example, glycerin (glycerol), propylene glycol and mixtures, thereof. The amount of solvent when used in the present compositions ranges from about 0.1% to about 25% by weight, preferably about 1% to about 15% by weight, even more preferably about 1.5% to about 10% by weight.

The present invention relates to an orally compatible, pleasant tasting composition in liquid form comprising:
 i. Ubiquinone or ubiquinol in an effective amount, preferably an effective amount within the range from about 0.05% to about 10% by weight of the composition;
 ii. An effective amount of a primary surfactant falling within the range of about 0.5% to about 35% by weight, preferably about 2% to about 25% by weight of the composition;
 iii. A triglyceride in an amount ranging from about 0.2% to about 50% by weight of the composition;
 iv. A phospholipid in an effective amount ranging from about 0.25% to about 20% by weight, preferably about 1% to about 10% by weight; and v. An amount of water ranging from about 1.0% to about 50% by weight, preferably about 2.5% to about 40–45% by weight.

Preferably, the compositions also comprise at least one sweetener in an amount ranging from about 0.05% to about 65% by weight. In addition, the present compositions may include one or more of the following: a solvent preferably selected from the group consisting of ethanol or a polyhydric alcohol such as glycerin and propylene glycol in amounts ranging from about 0.1% to about 25% by weight, more preferably about 0.5 to about 10% by weight, a secondary surfactant such as a Span™ surfactant preferably in an amount ranging from about 0.01% to about 7.5% by weight of the composition, a lipid soluble reducing agent (in the case where ubiquinol is included in the present compositions) in an amount ranging from about 0.1% to about 15%, more preferably about 1% to about 7.5% by weight and flavoring and coloring agents in minor amounts, generally ranging from about 0.005% to about 5% by weight of the final composition.

In certain embodiments according to the present invention, a pharmaceutically acceptable gelling agent or viscosity control agent, such as cellulose gelling agent (hydroxymethylcellulose, hydroxypropylcellulose, among others), guar gum, xanthan gum, etc., among numerous other Pharmaceutically acceptable gelling agents may also be added to the compositions in amounts ranging from about 0.005% to about 3.0% by weight in an effort to produce a final composition which exhibits increased viscosity. Pharmaceutically acceptable carriers, additives and excipients which are appropriate for oral dosage forms may also be included within the compositions according to the present invention Compositions according to the present invention are formulated in oral dosage form as a palatable, pleasant-tasting liquid, including a viscous liquid (i.e., having a viscosity in centipoise units which is consistent with the formation of a flowable gel). The compositions according to the present invention are generally taken by the subject orally, pursuant to an appropriate pharmaceutical regimen. The compositions according to the present invention, because of their enhanced palatability, dramatically improve patient compliance for the administration of ubiquinone/ubiquinol, especially in children.

To prepare the pharmaceutical compositions according to the present invention, an effective amount of ubiquinone or ubiquinol in powdered or liquid form is added to a mixture of phospholipid and triglycerides in combination with a polysorbate surfactant at elevated temperature. A solvent may be optionally added. After thorough mixing, the remaining components are added to the mixture and mixed to a uniform consistency. Sweetener, which generally includes water, is added last o the mixture, along with other components such as flavoring agents, colroing agents, presevatives and gelling agent, if applicable.

In alternative embodiments which include ubiquinol in combination with a reducing agent, a lipid soluble reducing agent is added to the ubiquinone in the triglycerides, phospholipids and surfactant, optionally in the presence of a solvent, at elevated temperature. This approach results in the reduction Of the ubiquinone to ubiquinol.

Although ubiquinol can be produced as a first step and then added to the other components in making oral dosage forms according to the present invention, the preferred method is to provide for the in situ preparation of ubiquinol from the less expensive and commercially available ubiquinone (ubiquinol is not commercially available) as described above. In a preferred method of preparing compositions according to the present invention wherein ubiquinol is obtained from coenzyme Q as the starting material, the components such as the triglycerides, phospholipids, surfactant and optional solvent and in certain embodiments, lipid soluble reducing agent, are first added together at elevated temperature (generally, at a temperature of about 45 8° C., preferably at a temperature of about 50–60° C.) until the components are thoroughly mired. At the point of thorough mixing at elevated temperature, the components are in a liquid state. Subsequent to mixing of the components, coenzyme Q is added to the mixture at elevated temperature as described above and throughly mixed into the above components fo[00f8] sufficient period. If the mixture to which the coenzyme Q is added contains an effective concentration of reducing agent, coenzyme Q will be converted to ubiquinol and the mixture can be used, upon further processing and addition of sweeteners, flavoring agents and the like to provide oral dosage forms which contain ubiquinol. In certain embodiments, aft r the coenzyme Q is added to other components, a reducing agent is thereafter added in an amount effective to convert the coenzyme Q to ubiquinol or alternatively, in an amount which not only is effective to convert coenzyme Q to ubiquinol, but also effective to maintain ubiquinol in its reduced state in a storage stable form. Additional reducing agent may be added to compositions according to the present invention at later steps in order to further promote the storage stability of the compositions.

The concentration of ubiquinone/ubiquinol to be included in the compositions according to the present invention is an effective amount for treating the patient's disease or condition. This concentration will depend on absorption, distribution, inactivation, and excretion rates of the ubiquinone/ubiquinol and its metabolites as well as other factors known to those of skill in the art. It is to be no that dosage values will also vary with the severity of the condition to be alleviated. It is t be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient, ubiquinone/ubiquinol, may be administered at once, or may be divided into a number of smaller doses to be administered at varying intervals of time.

The active components of the present invention can also be mixed with other active materials such as vitamin E (tocopherol s), alpha Lipoic acid, L-carnitine (and its derivatives acetyl-L-carnitine and propionyl-L-carnitine) and vitamins and minerals and other components, including omega-3-fatty a ids, among others, which do not impair their desired action, or with materials that supplement the desired action provided that the added materials do not change the activity of the included compounds.

Administration of the active is generally oral, from one to four times daily. The most effective dosage form will depend upon the pharmacokinetics of the particular agent chosen as well as the severity of the condition in the patient to be treated.

The present compositions are used to teat any number of disease states or conditions which respond to the administration of ubiquinone/ubiquinol. However, because the oral compositions increase the patient compliance of children, the treatment of childhood conditions or disease states will most likely find the greatest benefit in improved patient compliance using the compositions according to the present invention. The compositions according to the present invention are most preferably used to treat patients for heart disease, including congestive heart failure, hi blood pressure, mitochochondrial disorders, including mitochondrial encephalomyopathy and other mitochondrial cytopathies, anoxia, lactic acidosis, neurodegenerative diseases, Kearns-Sayre syndrome and Alper's disease. Most preferably, the patient is a child and the condition or disease state is mitochondrial cytopathy.

Having generally described the invention, reference is now made to the following examples which are intended to illustrate preferred embodiments and comparisons. The included examples are not to be construed as limiting the scope of this invention as is more broadly set forth above and in the appended claims.

EXAMPLE 1

Liquid Oral Dosage Form of Coenzyme $Q_{10}$

| Wt. Range | Typical Syrup Rx | w/w |
|---|---|---|
| (0.1–5.0%) | Coenzyme $Q_{10}$ | 2% |
| (2%–25%) | Tween 80 (Polysorbate 80) | 10% |
| (1%–10%) | Hydroxylated Lecithin | 5.75% |
| (5%–50%) | Medium Chain Triglycerides | 30.5% |
| (q/s 25–50%) | Syrup, USP | 48.0% |
| (q/s) | Flavorings and Sweeteners | 1.75% |
| (0.5%–10%) | Glycerine | 2.0% |

Procedure:
1. Add hydroxylated Lecithin to the Medium Chain Triglycerides in a jacketed mixing vessel. Heat to 130° F. (±5° F.) with constant stirring at 160° ±RPM for 2 hours o[00f8] until dissolved.
2. Add Tween 80 to the above solution with constant stirring while maintaining the temperature at 130° F. (±5° F.). Keep fixing for at least 60 minutes.
3. Now screen the $CoQ_{10}$ powder through a 100 mesh screen into the liquid blend while stirring and maintaining the temperature at 130° F. (±5° F.). Keep stirring until a clear solution is obtained (about 60 minutes to 90 minutes). Then add glycerine and stir for an additional 5 to 10 minutes.
4. Slowly add Syrup USP to the above $CoQ_{10}$ solution prepared above while mixing continuously and mantaining the temperature at 130° F. (±5° F.). Keep mixing for at least two hours.
5. Remove the source of heat. Keep mixing while the temperature of the composition comes down to 100° F. At this point, add the flavoring solution. Mix for two hours.
6. Filter finished syrup through a suit able filter.
7. Store syrup in an air and light resistant container.
8. Test for assay of $CoQ_{10}$, dissolution of $CoQ_{10}$, color ,clarity, flavor, sweetness, etc.

It is to be understood by those skilled in the art that the foregoing description and examples are illustrative of practicing the present invention, but are in no way limiting. Variations of the detail presented herein may be made without departing from the spirit and scope of the present invention as defined by the following claims.

What is claimed is:

1. An orally compatible, palatable composition in liquid dosage form comprising:

i. An active compound selected from the group consisting of ubiquinone, ubiquinol and mixtures thereof in an effective amount:

ii. An effective amount of a polysorbate surfactant falling within the range of about 0.5% to about 35% by weight;

iii. A triglyceride in an amount ranging from about 0.2% to about 50% by weight of the composition;

iv. A phospholipid in an effective amount ranging from about 0.25% to about 20% by weight;

v. A sweetener in an amount ranging from 0% to about 65% by weight; and vi. An amount of water ranging from about 1.0% to about 50% by weight.

2. The composition according to claim 1 wherein said primary surfactant is a polysorbate surfactant in an amount ranging from about 2% to about 25% by weight of said composition.

3. The composition according to claim 1 wherein said triglyceride is a mixture of medium chain triglycerides comprising about 5% to about 50% by weight of said composition.

4. The composition according to claim 1 wherein said phospholipid is selected from the group consisting of phosphatidylcholine, phosphatidylethanolamine, hydroxylated lecithin, distearoylphosphatidylcholine, phosphatidylserine, phosphatidylglycerol, phosphatidic acid, phosphatidylinositol, sphingomyelin, dimyristoylphosphatidylcholine, dimyristoylphosphatidylglycerol, and mixtures thereof and comprises about 1% to about 20% by weight of said composition.

5. The composition according to claim 4 wherein said phospholipid is hydroxylated lecithin in an amount ranging from about 1% to about 10% by weight.

6. The composition according to claim 1 wherein said sweetener is selected from the group consisting of aspartame, saccharin, cyclamates, sucralose, sucrose, maltose, sugar syrup, corn syrup, fructose syrup, fruit syrup sweeteners and sugar alcohols.

7. The composition according to claim 1 wherein said active agent is ubiquinone.

8. The composition according to claim 1 wherein said active agent is ubiquinol and said composition further comprises an effective amount of a lipid soluble reducing agent.

9. The composition according to claim 8 wherein said lipid soluble reducing agent is selected from the group consisting of α-tocopherol, tocopherol esters, ascorbate esters, α-carotene, β-carotene, lycopene, flavonoids, riboflavin, curcuminoids, retinol, retinoic acid, retinoic acid esters, retinol acetate, retinal and mixtures thereof.

10. The composition according to claim 1 further comprising an effective amount of at least one additional component selected from the group consisting of solvents, flavorings, coloring agents and a secondary surfactant.

11. The composition according to claim 10 wherein said solvent is selected from the group consisting of ethanol, glycerine, propylene glycol and mixtures thereof.

12. The composition according to claim 1 wherein said active agent is ubiquinone and further comprises at least one additional agent selected from the group consisting of tocopherols, alpha lipoic acid, L-carnitine, acetyl-L-carnitine, propionyl-L-carnitine, omega-3-fatty acids, vitamins, minerals and mixtures, thereof.

13. The composition according to claim 1 wherein said primary surfactant is polysorbate 80 in an amount ranging from about 2% to about 25% by weight of said composition, said triglyceride is a mixture of medium chain triglycerides comprising about 5% to about 50% by weight of said composition, said phospholipid is hydroxylated lecithin comprising about 1% to about 10% by weight of said composition, said sweetener is sucrose syrup, said active agent is coenzyme $Q_{10}$ and said composition further comprises a flavoring agent and a solvent which is glycerine in an amount ranging from about 0.5% to about 10% by weight of said composition.

14. The composition according to claim 9 wherein said ascorbate ester reducing agent is ascorbyl palmitate.

15. An orally compatible, pleasant tasting composition in liquid dosage form comprising:
   i. Coenzyme $Q_{10}$;
   ii. An effective amount of polysorbate surfactant ranging from about 2% to about 25% by weight;
   iii. A mixture of medium chain triglycerides ranging from about 5% to about 50% by weight of the composition;
   iv. Hydroxylated lecithin as phospholipid in an effective amount ranging from about 1.0% to about 10% by weight of said composition;
   v. Sugar syrup in an amount ranging from about 25% to about 50% by weight;
   vi An amount of water ranging from about 5.0% to about 45% by weight; and
   vii. An amount of glycerine ranging from about 0.5% to about 10% by weight of said composition.

16. The composition according to claim 15 further comprising a flavoring agent and at least one sweetening agent selected from the group consisting of aspartame, saccharin, cyclamates, sucralose, sucrose, maltose, sugar syrup, corn syrup, fructose syrup, fruit syrup sweeteners and sorbitol solutions.

17. The composition according to claim 16 further comprising a coloring agent.

18. A method of increasing the palatability of an orally administered dosage form of an active agent selected from the group consisting of ubiquinone, ubiquinol and mixtures thereof, said method comprising formulating into an oral liquid dosage form a composition comprising:
   i. An effective amount of said active agent;
   ii. An effective amount of a polysorbate surfactant falling within the range of about 0.5% to about 35% by weight;
   iii. A triglyceride in an amount ranging from about 0.2% to about 50% by weight of the composition;
   iv. A phospholipid in an effective amount ranging from about 0.25% to about 20% by weight;
   v. A sweetener in an amount ranging from 0% to about 65% by weight; and
   vi An amount of water ranging from about 1.0% to about 50% by weight.

19. The method according to claim 18 wherein said primary surfactant is a polysorbate surfactant in an amount ranging from about 2% to about 25% by weight of said composition.

20. The method according to claim 18 wherein said triglyceride is a mixture of medium chain triglycerides comprising about 5% to about 50% by weight of said composition.

21. The method according to claim 18 wherein said phospholipid is selected from the group consisting of phosphatidylcholine, phosphatidylethanolamine, hydroxylated lecithin, distearoylphosphatidylcholine, phosphatidylserine, phosphatidylglycerol, phosphatidic acid, phosphatidylinositol, sphingomyelin, dimyristoylphosphatidylcholine, dimyristoylphosphatidylglycerol, and mixtures thereof and comprises about 1% to about 20% by weight of said composition.

22. The method according to claim 21 wherein said phospholipid is hydroxylated lecithin in an amount ranging from about 1% to about 10% by weight.

23. The method according to claim 18 wherein said sweetener is selected from the group consisting of aspartame, saccharin, cyclamates, sucralose, sucrose, maltose, sugar syrup, corn syrup, fructose, fruit syrup sweeteners and sugar alcohols.

24. The method according to claim 18 wherein said active agent is ubiquinone.

25. The method according to claim 18 wherein said active agent is ubiquinol and said composition further comprises an effective amount of a lipid soluble reducing agent.

26. The method according to claim 25 wherein said lipid soluble reducing agent is selected from the group consisting of α-tocopherol, tocopherol esters, ascorbate esters, α-carotene, β-carotene, lycopene, flavonoids, riboflavin, curcuminoids, retinol, retinoic acid, retinoic acid esters, retinol acetate, retinal and mixtures thereof.

27. The method according to claim 18 wherein said composition further comprises an effective amount of at least one additional component selected from the group consisting of solvents, flavorings, coloring agents and a secondary surfactant.

28. The method according to claim 27 wherein said solvent is selected from the group consisting of ethanol, glycerine, propylene glycol and mixtures thereof.

29. The method according to claim 28 wherein said active agent is ubiquinone.

30. The method according to claim 18 wherein said primary surfactant is polysorbate 80 in an amount ranging from about 2% to about 25% by weight of said composition, said triglyceride is a mixture of medium chain triglycerides comprising about 5% to about 50% by weight of said composition, said phospholipid is hydroxylated lecithin comprising about 1% to about 10% by weight of said composition, said sweetener is sucrose syrup, said active agent is coenzyme $Q_{10}$ and said composition further comprises a flavoring agent and a solvent which is glycerine in an amount ranging from about 0.5% to about 10% by weight of said composition.

31. The composition according to claim 26 wherein said ascorbate ester reducing agent is ascorbyl palmitate.

32. A method of increasing the palatability of an orally administered dosage form of an active agent selected from the group consisting of ubiquinone and ubiquinol, said method comprising formulating into an oral liquid dosage form a composition comprising:
   i. An effective amount of Coenzyme $Q_{10}$;
   ii. An effective amount of a polysorbate surfactant ranging from about 2% to about 25% by weight;
   iii. A mixture of medium chain triglycerides ranging from about 5% to about 50% by weight of the composition;
   iv. Hydroxylated lecithin as phospholipid in an effective amount ranging from about 1.0% to about 10% by weight of said composition;
   v. Sugar syrup in an amount ranging from about 25% to about 50% by weight;
   vi An amount of water ranging from about 5.0% to about 45% by weight; and
   vii. An amount of glycerine ranging from about 0.5% to about 10% by weight of said composition.

33. The method according to claim 32 wherein said surfactant is polysorbate 80.

34. The method according to claim 32 wherein said composition further comprises a flavoring agent and at least one sweetening agent selected from the group consisting of aspartame, saccharin, cyclamates, sucralose, sucrose, maltose, sugar syrup, corn syrup, fructose syrup, fruit syrup sweeteners and sugar alcohols.

35. The method according to claim 34 wherein said composition further comprises a coloring agent.

* * * * *